United States Patent [19]

Holy et al.

[11] Patent Number: 5,457,144
[45] Date of Patent: Oct. 10, 1995

[54] DEGRADABLE POLYAMIDES

[75] Inventors: Norman L. Holy, Penn Park; Newman M. Bortnick, Oreland, both of Pa.

[73] Assignee: Rohm and Haas Company, Philadelphia, Pa.

[21] Appl. No.: 115,534

[22] Filed: Feb. 2, 1994

Related U.S. Application Data

[63] Continuation-in-part of Ser. No. 847,969, Mar. 6, 1992, abandoned.

[51] Int. Cl.⁶ .................................. C08K 5/15; C08K 5/11
[52] U.S. Cl. .................. 524/108; 523/124; 523/125; 523/128; 524/310; 524/314; 524/321; 524/279; 525/411; 525/415; 525/425; 525/432; 528/279; 528/324; 528/329.1; 528/341; 528/343
[58] Field of Search .................................. 524/314, 108, 524/310, 321; 523/128, 124, 125; 525/411, 415, 425, 432; 528/324, 329.1, 341, 343, 279

[56] References Cited

U.S. PATENT DOCUMENTS

| | | | |
|---|---|---|---|
| Re. 30,170 | 12/1979 | Goodman et al. | |
| 2,989,364 | 6/1961 | Goldann. | |
| 3,328,341 | 6/1967 | Corbin et al. | |
| 3,592,873 | 7/1971 | Ishida et al. | |
| 3,758,631 | 9/1973 | Werner et al. | 525/411 |
| 3,781,381 | 12/1973 | Koleske et al. | |
| 3,790,531 | 2/1974 | Christoph et al. | 528/343 |
| 3,850,862 | 11/1974 | Clendinning et al. | 523/128 |
| 3,850,863 | 11/1974 | Clendinning | 523/128 |
| 4,209,660 | 6/1980 | Shalaby et al. | |
| 4,459,394 | 7/1984 | Coffey et al. | 528/319 |
| 4,476,255 | 10/1984 | Bailey et al. | |
| 4,595,747 | 6/1986 | Gabbert | 528/319 |
| 4,835,248 | 5/1989 | Bader et al. | |
| 5,140,095 | 8/1992 | Guaita et al. | 528/324 |
| 5,223,603 | 6/1993 | Patton et al. | 528/343 |
| 5,272,221 | 12/1993 | Kitao et al. | |
| 5,300,576 | 4/1994 | Nemphos et al. | 525/450 |
| 5,310,599 | 5/1994 | Ford | 525/415 |

FOREIGN PATENT DOCUMENTS

| | | |
|---|---|---|
| 1142297 | 2/1969 | European Pat. Off. |
| 409093 | 1/1991 | European Pat. Off. |
| 54-11959 | 9/1979 | Japan. |
| 54-119595 | 9/1979 | Japan. |
| 56-02232 | 3/1981 | Japan. |
| 1099456 | 1/1968 | United Kingdom. |

OTHER PUBLICATIONS

J. Appl. Polymer Sci., 24(7), 1701–11 (1979).
Eur. Polym. J., 529–557 (1984).
Chemtech, 21, 26–30 (1991).
Polymers and Ecological Problems—J. Guillet et al 61–79 (1973) vol. 3 of Polymer Science & Technology, Plenum Press, N.Y.
Modern Plastics Encyclopedia pp. 30 and 31 (1989).

*Primary Examiner*—Veronica P. Hoke
*Attorney, Agent, or Firm*—Joseph F. Leightner

[57] ABSTRACT

This invention provides hydrolytically labile polyamide compositions and articles containing an ester derived moiety in the polymer backbone which will degrade after exposure to water over long periods of time.

11 Claims, No Drawings

DEGRADABLE POLYAMIDES

STATUS OF RELATED APPLICATIONS

This application is a continuation-in part of U.S. Ser. No. 07/847,969 filed Mar. 6, 1992, now abandoned.

BACKGROUND OF THE INVENTION

This invention relates to polyamide polymers which become brittle after long exposure to moisture, and to blends of such polyamides and certain water soluble polymers which rapidly lose mechanical properties when exposed to moisture. It also relates to use of such polymers as degradable monofilament, fibers, degradable plastic articles, and degradable films. It further relates to the use of such polymers in biological implants.

Japanese Kokai No. 56 022324 describes the production of alternate block copolymers of low molecular weight aliphatic polyesters and low molecular weight aliphatic polyamides, by ester-amide interchange, which are useful for mulch films biodegradable via enzyme digestion (*Rhizopus delemar* lipase). In this polymer, the polyester to polyamide ratio is high in polyester, for example, 4 to 1 mole per cent polyester to nylon 6.

Japanese Kokai No. 54 119594 describes the production of a biodegradable low molecular weight aliphatic polyester amide alternate block copolymer from polycaprolactone and nylon 6 in the presence of zinc acetate. The polyester to polyamide ratio is near 1 to 1. Again, the product polymer is subject to enzymatic (lipase) degradation.

Japanese Kokai No. 54 120727 describes polyester polyamide block copolymers, high in the polyester component, which are useful for production of biodegradable films or fibers. There is no mention of marine uses of the copolymers.

U.S. Pat. No. 3,592,873 describes the preparation of polyamide esters as interpolymers to provide thermal stability in polyoxymethylenes. The polyamide esters are prepared by reacting lactams or alkyl substituted lactams with at least a four membered ring with lactones or alkyl substituted lactones, again with at least a four membered ring.

*J. Appl. Polymer Sci.*, 24(7), 1701–11 (1979) describes the synthesis of copolyamide-esters via amide ester interchange of polycaprolactone with nylon 6, 66, 69, 11, 12, or 612. It also describes biodegradation of the polymers by *Rhizopus delemar* lipase digestion or alcoholic alkali hydrolysis. The effect of nylon/polycaprolactone ratio on the biodegradability was examined and biodegradability was found to decrease as the polycaprolactone content decreased. Furthermore, biodegradability was also found to decrease as the length of the polyamide blocks shortened. Copolyamide-esters with less than about 20% ester content were found to be non-biodegradable.

*Eur. Polym. J.*, 529–557 (1984) describes the preparation of copolyesteramides by anionic ring opening copolymerization of $\epsilon$-caprolactam with $\epsilon$-caprolactone. Alternating copolymers or random multiblock copolymers with amide to ester ratios of 90/10 to 10/90 were prepared. In addition, the reference describes cleavage by alkaline hydrolysis as well as tensile properties of films and fibers fabricated from the copolymers.

*Chemtech*, 21, 26–30 (January, 1991) describes the biodegradability of a variety of commercial plastics and compares their utility for medical applications. Medical uses are related to mechanical and degradative properties of many of the commercial materials.

The combination of properties which polyamides exhibit make them ideal for use in fibers. The term "polyamide" in this application includes any aliphatic or cycloaliphatic polyamide. Such materials are known commercially as nylons. Nylon fibers have many properties which make them ideal for use in netting, including strength, light weight, and resistance to degradation, However, some of these desirable properties also result in a significant environmental problem. The lifetime for nylon netting in the ocean has been estimated as over ten years, and may be closer to thirty years. Netting which has either been abandoned intentionally or by accident continues to capture marine fish and mammals. These "ghost" nets account for enormous kills of fish, seals, whales, and dolphins. Seal deaths alone are estimated to be about 40,000 annually world wide. A similar situation is found in abandoned lobster traps where any captured lobsters are unable to free themselves from the trap's netting. Analogous situations exist in fresh water lakes, many being contaminated with fishing line either lost or abandoned.

Commercial nylons are also used in biological implants. However, because of their biological inertness, uses are limited to those in which the implant is permanent or in which it can be mechanically removed.

Polymers of lactic acid are well-known for their degradability under microbial attack. A copolyester of lactic and glycolic acids is used as a biodegradable suture in repairing soft tissue wounds. These polymers have also been used to fabricate degradable bone plate which is used to reinforce a broken bone during its healing period. There is no record of lactic acid/nylon copolymers being used in a similar manner.

Oxalate substitution for adipate units in nylon 66, or similar units in other bi-directional polyamides for the purpose of rendering the material more degradable is not reported. Oxalate esters are highly reactive hydrolytically. Thus, incorporation of oxalate units into nylon provides sites for attack and chain cleavage, whether biologically or by simple hydrolysis.

It is an object of this invention to create a degradable nylon which will degrade at a controlled rate in fresh water, ocean water, or other humid environments. It is a further object of this invention to create a degradable nylon useful for biological implants. Another objective is to create a degradable nylon film. A still further object is to provide a process for the efficient production of the degradable nylon.

SUMMARY OF THE INVENTION

These objects and others as will become apparent from the following disclosure are achieved by the present invention which involves incorporating into a nylon, or reacting with a nylon precursor, an appropriate ester, cyclic ester, or polyester such that the ester derived moiety is incorporated into the polymer backbone. Incorporation can be accomplished via three major routes; reaction of preformed polymers, for example, nylon 6 with polycaprolactone; reaction of a prepolymer with a monomer, for example, nylon 6 with dimethylglycolide; or copolymerization of two monomers, for example, caprolactam with caprolactone.

We have discovered that by controlling the extent and randomness of incorporation, the desirable properties of the nylon are largely maintained while at the same time the nylon becomes subject to hydrolysis by water, presumably at the incorporated ester functionality. Both the extent and randomness are controlled by the polymerization conditions.

These ester units, which are hydrolytically unstable, act as weak links. The strength of the nondegradable nylon is preserved. However, as the ester units are hydrolyzed, the chain is randomly cleaved to lower molecular weight fragments. The hydrolysis may be uncatalyzed, catalyzed by acids or bases, or biologically catalyzed. Furthermore, since the hydrolysis results in creation of an acidic polymer end group, it can also be autocatalyzed. Thus, the nylon becomes degradable as a result of hydrolysis of these hydrolytically labile weak links.

As the polymer chain length becomes shorter due to the hydrolytic degradation, the nylon becomes embrittled because the chain length becomes less than the length required for entanglement with adjacent chains. Thus, netting produced from ester modified nylon fibers becomes so weak over time that the struggles of a captured animal are sufficient to break the fiber, freeing the animal; biological implants degrade at a rate commensurate with their replacement by normal tissue; and films degrade at a predetermined rate.

DETAILED DESCRIPTION

The hydrolytically labile polyamides of this invention comprise: from about 80 to about 99.9 weight percent of a polyamide, such as nylon, including nylons 6, 6/6, 6/12, 6/9, 6/10, 11, 12, 4/12, 12/12, and the like; and from about 0.1 to about 20 weight percent of ester moieties selected and formed from an oxalate of formula I (bidirectional esters) or a dimethylglycolide of formula II (unidirectional esters):

$$R^1O-\underset{\underset{O}{\|}}{C}-\underset{\underset{O}{\|}}{C}-OR^2 \qquad \text{I}$$

$$\text{II}$$

(cyclic diester structure with $R^1$ and $R^2$ substituents)

wherein $R^1$ and $R^2$ are the same or different radicals selected from hydrogen or $C_1$–$C_{20}$ alkyl such as, for example, dibutyl oxalate, dimethyl oxalate, lactic acid cyclic dimer, and the like. The oxalate ester can also be in the form of a polymer (that is, the $R^1$ and $R^2$ radicals form connecting links between oxalate units). Examples of these polymeric oxalates include those wherein $R^1$ and $R^2$ are derived from ethylene glycol, propylene glycol, 1,4-butanediol, and the like. The oxalate, oxalate polymer, or glycolide dimer components are randomly incorporated into the polyamide chain as single, diad, triad, or oligomeric units. This invention also includes degradable articles prepared from polyamides which have been made hydrolytically labile by randomly incorporating into the polymer chains of the polyamide, singularly or in combination ester moieties from about 0.1 to about 20 weight percent of an alkyl ester. The alkyl ester is selected from compounds of the formula III, IV, V, or VI;

$$HO-(CR^1R^2)_n-\underset{\underset{O}{\|}}{C}-OR^3 \qquad \text{III}$$

$$+(CR^1R^2)_n-\underset{\underset{O}{\|}}{C}-O+_{\overline{x}} \qquad \text{IV}$$

$$(CR^1R^2)_m-\underset{\underset{O}{\|}}{C}\underset{O}{\overset{O}{\diagup}} \qquad \text{V}$$

$$R^3O-\underset{\underset{O}{\|}}{C}-(CR^1R^2)_n-\underset{\underset{O}{\|}}{C}-OR^3 \qquad \text{VI}$$

wherein $R^1$ and $R^2$ are the same or different radicals selected from H, or $C_1$–$C_4$ alkyl; $R^3$ is selected from hydrogen or $C_1$–$C_{20}$ alkyl; n is 1–10; m is 2–6; and x varies with the polymer molecular weight range; such as, for example, 3-hydroxybutyric esters, polycaprolactone, caprolactone, adipic esters, and the like. Furthermore, the invention includes copolymers of amide and ester functionality such as, for example, compositions derived from caprolactam with caprolactone, caprolactam with dimethylglycolide, adipic ester and hexamethylenediamine with dimethyl oxalate, and the like.

The polyamides of this invention include any of the materials typically referred to as nylons, both bi-directional (produced from dibasic acids and diamines) and unidirectional (produced from amino-substituted acids or lactams). Lactam monomers can also be used. Similarly, the ester can be bi-directional such as, for example, dimethyl adipate, dibutyl oxalate, oxalic acid polymers such as those with ethylene glycol, propylene glycol, or 1,4-butanediol, or the ester can be unidirectional, such as caprolactone or a polyester, such as polycaprolactone, polylactic acid, polyglycolic acid, or poly-3-hydroxybutyrate. Acids, esters, or polymers of α, β, or higher, hydroxy-substituted carboxylic acids can also be used. The ester can also be in the form of a glycolide, such as dimethylglycolide. The ester can be incorporated at up to 20 weight percent without substantially and negatively affecting the desirable properties of the nylon. In fact, at lower levels within this range, the strength of the degradable nylon actually exceeds that of corresponding unmodified nylon. This finding was completely unexpected. Ester levels of one to ten weight percent are preferred depending upon the degradation time desired.

Despite the presence of the hydrolytically labile ester functionality, we have found that the degradable nylon can be prepared using standard techniques known to those skilled in the art for preparation of commercially available nylons including water catalyzed copolymerization of caprolactam and caprolactone and anionic copolymerization, when these techniques are modified as described in this application. The degradable nylon can also be prepared using an ester-amide interchange reaction.

The ester-amide interchange or derivatization is readily accomplished in a melt. Melt temperatures can be in the range of about 180° C. to about 300° C. Preferred melt temperatures vary with the ester to be incorporated. For example, from about 240° C. to about 290° C. is preferred for polycaprolactone while from about 200° C. to about 220° C. is preferred for dimethylglycolide. In the case of extrusion, ester incorporation is dependent on the extent of mixing and the residence time in the extruder. Twin-screw extruders are generally preferred over single-screw extruders because of the greater extent of mixing. Even though the reaction is not a transesterification, it can be catalyzed by non-protic acidic transesterification catalysts, such as tin octoate or zirconium acetylacetonate, or the like. It can also be catalyzed by anionic catalysts, such as lithium or sodium t-butoxide; sodium or lithium hydride; sodium or potassium methoxide or ethoxide; sodium amides; sodium salts of $C_1$–$C_6$ alkyl substituted mono and diamines and the like.

When lactam monomers are used it can be catalyzed by their sodium or potassium salts. For acid catalyzed incorporation, the most preferred catalyst is zirconium acetylacetonate which we have found to be unexpectedly efficient in reducing the time required for incorporation of the ester into the polyamide. Catalyst levels of 0.001% to about 0.5% can be used. However, levels of about 0.05% to about 0.2% are preferred. Most preferred is a level of about 0.1%.

Water catalyzed production of copolymers of caprolactam and caprolactone has been reported in GB 1,009,456. However, the GB 1,009,456 process and requires excessive process time (13–14 hour reaction time and a total process time of 19–21 hours). We have found that by increasing the temperature to from about 260° C. to about 300° C., preferably from about 275° C. to about 285° C., and with water levels of from about 3 weight percent to about 15 weight percent of the total caprolactam plus caprolactone weight, the reaction time is reduced to a commercially acceptable 1–2 hours. Furthermore, the molecular weight of the copolymer is sufficient to provide desirable properties.

Although anionic copolymerization methods for producing copolyester-amides are also reported, we have found that the copolymers produced are invariably of low molecular weight, so low that the melt viscosity is insufficient for extrusion into a material such as a monofilament fiber. We have discovered that when the process is conducted under the conditions of this invention, higher molecular weight material is produced. We have also discovered that when from about 0.01 weight percent to about 0.2 weight percent of graft or crosslinking agents, for example, triamines, such as commercially available polyoxypropylene triamines are added anytime during the polymerization or anhydrides, such as maleic, succinic, and phthalic anhydrides, are added after the polymerization is largely completed, that the melt viscosity is markedly enhanced over known processes. Other known nylon graft or cross-linking agents such as all acrylic, or methacrylate-butadieneostyrene impact modifiers or polyglutarimides or polymers containing anhydrides may also act as melt viscosity enhancers.

The final polymer compositions can include typical additives known in the art, for example; impact modifiers such as ABS (acrylonitrile/butadiene/styrene), MBS (methyl methacrylate/butadiene/styrene), all acrylic types, and the like; fillers such as hydrated alumina, glass or other fiber reinforcements, talc or other minerals, metallic particles, and the like; colorants (e.g. pigments and dyes), toners, and color agents or concentrates such as those described in the Color Index (Society of Dyers and Colourists, U.S.A.), including Pigment Black 7, Pigment White 6, Pigment White 21, Pigment Green 7, Pigment Blue 15, Solvent Orange 60, Solvent Red 179, Solvent Green 28, Solvent Blue 45, Solvent Blue 101, Solvent Violet 14, Disperse Yellow 54, toner Irisol N™ (1-p-toluidino-4-hydroxyanthraquinone), and the like; lubricants such as high molecular weight alcohols (such as those with 12–24 carbons), esters (especially long-chain alkyl esters of high molecular weight acids including butyl or stearyl stearate), monoesters of glycols (such as ethylene glycol monostearate), and the like; antioxidants such as organophosphites (such as tris(aryl)- or tris(alkylaryl)- or tris(alkyl)phosphites), organophosphonites (such as trisaryl-, trisalkaryl-, or aryldialkaryl-phosphonites); thioesters (such as dilauryl thiodipropionate, ditridecyl thiodipropionate, and distearyl thiodipropionate), and the like; and ultraviolet stabilizers such as hydroxybenzophenones, salicylate esters, benzotriazoles, hindered amines [such as bis-(2,2,6,6-tetramethyl-4-piperidinyl)sebacate, 2,2,6,6 -tetramethyl-4-piperidinyl benzoate, 1,2,3,4- tetrakis-(2,2,6,6-tetramethyl-4-piperidinyl)butane-tetracarboxylate, 1,2-bis-(2-oxo-3,3,5,5-tetramethyl-1-piperidinyl)ethane, 1-(3,5-di-tert-butyl-4-hydroxyphenyl)-2, 2-bis-(2,2,6,6-tetramethyl-4-piperidinyloxycarbonyl)hexane, poly(1-oxyethylene-(2,2,6, 6-tetramethyl-1,4 -piperidinyl)-oxysuccinyl, N,N'-bis-(2,2, 6,6-tetramethyl-4-piperidinyl)-1,6-hexanediamine, and bis-(4 -hydroxy-2,2,6,6-tetramethyl-1-piperidinyl)ethane, and the like; blowing agents; flatting agents; antistatic agents; conductive materials; odor control agents; and the like.

In addition, for items discarded on land, a hydrolytic mechanism of degradation may not be entirely effective simply because of a lack of sufficient humidity or water to promote degradation at an appropriate rate. To enhance degradation under these conditions, a photosensitizer may be added to the degradable nylon. Photochemically active organic materials such as, for example, benzophenone, Rose Bengal; iron or cobalt phthalocyanines, and the like, or inorganic salts, such as salts of iron, nickel, cobalt, and the like, may be added.

The degradable nylons of the present invention are ideally suited for fabrication into articles which depend on the nylons' desirable properties, such as, for example, high strength, flexibility, light weight, and the like, but where nylon use had been discouraged due to disposal problems related to the non-degradable nature of nylon.

In one embodiment of the present invention articles are fabricated from degradable monofilament or multifilament nylon fibers. Such articles include but are not limited to fish netting; fishing line; rope; netting for crab and lobster pots; long lines; grass trimmer lines; net mats for collection of waste such as yard or lawn waste, grass clippings, and leaves; net mats for replacement of geotextiles used in control of soil erosion; laces for shoes, bags, and the like; fabrics for making articles such as diaper front panels, sneakers, running shoes, backpacks and other bags; netting for containing root bases for transplanting trees and shrubs; and the like. Such degradable articles are desirable from a number of perspectives. First, articles fabricated entirely from degradable nylon, especially articles such as fishing line or netting when lost in the environment will degrade rather than persist. Secondly, articles to contain other waste, such as lawn or yard waste, can be disposed of with the waste itself and will degrade concurrently with it, particularly in warm humid environments such as those which occur during composting. In addition, such articles can be placed under waste producing objects to capture waste as it is produced. Thirdly, when used with other components in combination in articles that wear out, such as, for example, in fabric uppers for sneakers or running shoes, when the articles are discarded, the fabric will degrade. Fourthly, the articles can be used as a carrier or support for controlled delivery of other materials into the environment such as, for example, incorporating a seed tape and/or fertilizer tape into an erosion control net mat would provide the advantage of mechanical erosion control with the net mat until sufficient foliage is established followed by degradation of the net mat.

Another embodiment of the present invention relates to articles fabricated from degradable nylon film, especially blown film. One advantage of such a degradable nylon film is that it may replace film currently using polymers which are not degradable but were previously used because of their cost advantage over nylon; even though the nylon may have had a physical property advantage over currently used materials. Such articles include, but are not limited to, bags such as garbage, grocery, produce, yard waste, trash bags, and the like; mulch and garden films; disposable diaper back panels; feed bags; packaging films; "six-pack" loop carriers and the like.

A third embodiment of the present invention includes molded articles and blown bottles which have a limited lifetime, and which would be more environmentally acceptable if they degraded after disposal. Such molded articles include, but are not limited to, toiletry items such as toothbrushes, disposable razors, tampon applicators, brushes, combs, and the like; sporting goods such as gun stock frames, clips, and the like; pads and protectors such as forearm, shoulder, hip, thigh, and shin guards, motorcycle "leathers", and the like; office supplies such as pens, housings for calculators, computers, telephones, fax machines, copiers, printers, keyboards, audio and video equipment, and the like; household items such as spools, laundry baskets, eyeglass frames, soap dispensers, dinnerware, cups, eating utensils, and the like; packaging materials such as milk crates, meat trays, produce trays, and the like; and gardening items such as seedling cones, and the like.

A fourth embodiment of the present invention includes articles for which rapid environmental degradation is desired, for example, over a period of less than one month. In these cases, the degradable nylon is blended with up to about 90 weight percent of a water soluble polymer such as, for example, poly(vinyl alcohol), and the like with a processing aid as described below. By "poly(vinyl alcohol)", often abbreviated "PVOH", is meant polymers made up predominately, that is at least about 85 mol percent, of units of the structure

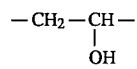

and generally prepared by the total or almost total hydrolysis of homopolymers of vinyl acetate or related vinyl esters, the starting polymer made up of units of the structure

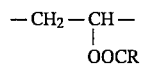

where R is alkyl, that is, from one to eight carbon atoms, preferably methyl. Such polymers are relatively insoluble in cold water, but dissolve rapidly in hot water. Melting of PVOH, such as in melt processing, is generally accompanied by severe thermal degradation. Most PVOHs when melt processed either contain a plasticizer, such as glycerol, or a processing aid that enables melt processing, such as those taught in LaFleur et al., U.S. Pat. No. 5,189,097, incorporated by reference. Such articles include, but are not limited to, articles which may be disposed of by composting, such as, disposable diaper front and back panels, grabage, grocery, and trash bags, and the like.

A fifth embodiment of the invention involves fabrication of biological and medical devices which require both degradability and high strength. Such articles include, but are not limited to "leave in" sutures; syringes; bone plates, screws, pins, nails, and the like; bone repair prosthetics which erode at rates comparable to bone regrowth; polymer matrix for tissue regrowth; and the like.

This invention is not to be construed as limited to any particular method of preparing the fibers, netting, film, molded articles, blown bottles or implants.

EXAMPLES 1 TO 6—UNIDIRECTIONAL POLYMER

Pellets of commercially available nylon 6 (Capron®8207; Allied Chemical Co.) were combined with dimethylglycolide (DMG) and extruded by means of a Leistritz twin-screw extruder. The mixtures were extruded in a single pass. The amounts of each component used are found in Table 1.

TABLE 1

| Ex. No | Nylon 6 | | DMG | | Catalyst | |
|---|---|---|---|---|---|---|
| | g. | % | g. | % | g. | % |
| 1 | 1500 | 100 | — | — | — | — |
| 2 | 1485 | 99 | 15 | 1 | — | — |
| 3 | 1455 | 97 | 45 | 3 | — | — |
| 4 | 1410 | 94 | 90 | 6 | — | — |
| 5 | 1453.5 | 96.9 | 45 | 3 | 1.5 | 0.1 |

Catalyst = Zirconium acetylacetonate

Extruded strands were pelletized and the pellets were then injection molded into notched Izod bars. The Izod bars were exposed to 60° C. sea water for periods of 7, 14, 21, 35, or 60 days and then tested for brittleness (Izod). Test results are in Table 2.

TABLE 2

| | | NOTCHED IZOD BEHAVIOR Units = ft. lbs./inch of notch | | | | | | | | |
|---|---|---|---|---|---|---|---|---|---|---|
| | | Day | | | | | | | | |
| Ex. No. | H/C | 7 % | | 14 % | | 21 % | | 35 % | | 60 % | |
| 1 | H | 100 | 24.00 | 100 | 24.52 | 100 | 23.29 | 80 | 24.74 | 100 | 24.65 |
| | C | | | | | | | 20 | 3.49 | | |
| 2 | H | 100 | 22.97 | 100 | 24.07 | 100 | 23.64 | 20 | 23.38 | 20 | 23.70 |
| | C | | | | | | | 80 | 7.85 | 80 | 2.65 |
| 3 | H | 100 | 22.65 | 80 | 23.29 | 40 | 21.72 | 60 | 22.21 | 40 | 23.11 |
| | C | | | 20 | 4.28 | 60 | 3.59 | 40 | 3.14 | 60 | 1.85 |
| 4 | H | 60 | 16.77 | 40 | 21.01 | | | | | | |
| | C | 40 | 3.80 | 60 | 3.37 | 100 | 2.35 | 100 | 3.06 | 100 | 1.27 |
| 5 | H | 100 | 20.90 | 40 | 17.63 | | | | | | |
| | C | | | 60 | 5.07 | 100 | 3.54 | 100 | 2.80 | 100 | 3.68 |

H = hinged break
C = clean break

TEST INTERPRETATION

Example 1, which is unmodified nylon 6, shows almost no change in notched Izod results over the course of 60 days immersion in 60° C. sea water.

However, copolymers formed by incorporation of dimethylglycolide into nylon 6 show switch from hinged to clean breaks in notched Izod tests. These results are consistent with a material which gradually becomes embrittled.

EXAMPLE 7—BIDIRECTIONAL POLYMER

Dimethyl adipate (1 part), 1,6-hexanediamine (1.1 parts), and dimethyl oxalate (0.1 parts) were combined in a round bottom flask and then heated to 100° C. The mixture was stirred while methanol formed during reaction was allowed to distill off slowly. When methanol distillation ceased, the temperature of the mixture was increased to 125° C. Upon cooling a solid polymer was obtained.

EXAMPLE 8—CATALYST EFFECT ON ESTER INCORPORATION

Nylon 6 (9 parts), polycaprolactone (1 part), and a catalyst (0.01 parts), all parts by weight, were combined and heated rapidly to 270° C. The temperature was then held constant at 270° C. Samples were periodically withdrawn and analyzed by differential scanning calorimetry (DSC). Over time, the peak in the DSC plot due to polycaprolactone diminished and finally disappeared, reflecting full incorporation of the polycaprolactone into the nylon 6 backbone. Time to full incorporation, that is, disappearance of the polycaprolactone peak, for three different catalysts is in Table 3. The significant advantage of the zirconium acetylacetonate catalyst is apparent.

TABLE 3

| Catalyst | Time to Full Incorporation |
| --- | --- |
| Tin(II) octoate | >4 hours |
| Zinc acetate | >3 hours |
| Zirconium acetylacetonate | 1.5–2 hours |

EXAMPLE 9—WATER CATALYZED COPOLYMERIZATION

Caprolactam (2178 pounds), caprolactone (22 pounds, 1.0 weight percent of the total of caprolactam plus caprolactone), and water (125 pounds) were combined in a reaction kettle. The temperature was raised to 275° C., resulting in a pressure of about 100 pounds per square inch. The system was first vented, and then placed under vacuum for 2.5 hours at a temperature of 270° C. The relative viscoscity of the material at this point was sufficiently high to make monofilament. The material was pelletized and then dried. The pellets were drawn into monofilament using standard commercial monofilament producing equipment. Draw stands were; first draw, 37.6; second draw, 150.2; third draw, 87.8; and forth draw, 175.0. The overall draw ratio was 4.66, the maximum was 5.0. The monofilament had a diameter of 24 mil and a breaking strength of 50 pounds. Nylon 6 produced at a comparable draw ratio has a breaking strength of 41–50 pounds. A similar degradable nylon with 1.5 weight percent caprolactone was also produced. The tensile properties of the two degradable nylons were compared to commercially available nylon 6. The data obtained were as follows:

| MATERIAL | % ELONGATION AT BREAK | LOAD AT BREAK POUNDS | STRESS AT BREAK IN POUNDS PER SQUARE INCH |
| --- | --- | --- | --- |
| Nylon 6 | 350 | 138 | 11,000 |
| 1.0% caprolactone | 325 | 140 | 12,000 |
| 1.5% caprolactone | 300 | 150 | 12,000 |

EXAMPLE 10—ANION CATALYZED COPOLYMERIZATION

Caprolactam (100 g.) and sodium methoxide (0.5 g. of a 25% by weight methanol solution) were combined in a round bottom flask and heated to 225° C. Rapid polymerization occurred indicated by a sharp increase in viscosity. Caprolactone (10 g.) was then added. The mixture was heated to 240° C. and stirred for 40 minutes and then poured from the flask. When cooled, the material had the appearance of normal nylon 6.

EXAMPLE 11—COMPARISON TO J. APPL. POLYMER SCI., 24(7), 1701–711 (1979)

Nylon 6 and polycaprolactone in a 90:10 ratio were reacted using the procedure of Tokiwa using zinc acetate catalyst, a temperature of 250° C., for one hour. An identical blend was reacted using the zirconium catalyst of this invention. The products from both reactions were molded into tensile and Izod bars, the bars were immersed in 70° C. water for either two days, one week, or two weeks, and then tensile and Izod tests were conducted. The results of these tests are as follows:

| Example* | a | b | c | d | e | f |
| --- | --- | --- | --- | --- | --- | --- |
| Time | 2 days | 2 days | 1 week | 1 week | 2 week | 2 week |
| Catalyst | Zn | Zr | Zn | Zr | Zn | Zr |
| Tensile | | | | | | |
| Elong. @ Max | 3.4% | 55.6% | 5.1% | 22.0% | 0.9% | 8.9% |
| Elong. @ Break | 3.4% | 147.6% | 5.1% | 79.0% | 0.9% | 8.9% |
| Load @ Max | 35.0 lbs | 69.3 lbs | 40.3 lbs | 71.7 lbs | 12.6 lbs | 57.2 lbs |
| Load @ Break | 35.0 lbs | 59.7 lbs | 40.3 lbs | 65.4 lbs | 12.6 lbs | 57.2 lbs |
| Stress @ Max | 2558 psi | 5236 psi | 3000 psi | 5602 psi | 919 psi | 4260 psi |
| Stress @ Break | 2558 psi | 4499 psi | 3000 psi | 5120 psi | 919 psi | 4260 psi |
| Notched Izod | 0.19 | 1.35 | 0.18 | 1.33 | 0.18 | 0.37 |

*Examples a, c, and e are from J. Appl. Polymer Sci.; b, d, and f from this invention.

These results show that material produced under the conditions of Tokiwa is initially more brittle and than material produced under the conditions of this invention. The results are consistent with the conclusion that under the conditions of Tokiwa polycaprolactone is not fully incorporated into the polyamide chain, that is, there are either large blocks of polycaprolactone within the polyamide chain or large quantities of unreacted polycaprolactone.

EXAMPLE 12—BLOWN FILM

The 1.5% caprolactone material from example 9 was combined with acrylic modified poly(vinyl alcohol), a segmented polymer prepared by acid catalyzed esterification onto an 88% hydrolized poly (vinyl alcohol) backbone of 4% by weight of a methyl methacrylate/N-vinyl pyrrolidone/ ethyl acrylate/methacrylic acid 55/25/18/2 polymer, in a research scale twin-screw blown film extruder, at a ratio of 80:20 by weight, and then blown into a film. The blow-up ratio was 8:1 resulting in a film thickness of 0.0007 inches (0.7 mil). The film was then tested for tensile properties with the following results: elongation at break=1351%; Stress at break=5500 pounds per square inch.

We claim:

1. A method comprising melt blending in the presence of a zirconium acetylacetonate catalyst:
   a) from about 80 to about 99.9 weight percent of a polyamide, and
   b) from about 0.1 to about 20 weight percent of one or more esters selected from the group consisting of:
      1) oxalates having the formula:

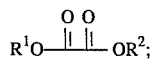

2) an oligomer formed from the reaction of oxalic acid and an alkylene glycol; and
      3) glycolides having the formula:

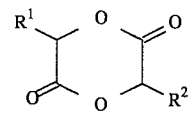

wherein $R^1$ and $R^2$ are the same or different radicals selected from hydrogen or $C_1$–$C_{20}$ alkyl; to form a hydrolytically labile polyamide composition wherein one or more esters are randomly incorporated into the polyamide backbone.

2. The method of claim 1 further comprising adding a photochemically active material to the hydrolytically labile polyamide.

3. The method of claim 1 further comprising adding an impact modifier to the hydrolytically labile polyamide.

4. The method of claim 1 further comprising forming a monofilament fiber from the hydrolytically labile polyamide.

5. The method of claim 1 further comprising forming a multifilament fiber from the hydrolytically labile polyamide.

6. The method of claim 1 further comprising forming a blown film from the hydrolytically labile polyamide.

7. The method of claim 1 further comprising forming a molded article from the hydrolytically labile polyamide.

8. The method of claim 1 further comprising forming a blown bottle from the hydrolytically labile polyamide.

9. The method of claim 1 wherein the ester is selected from the group consisting of dibutyl oxalate, dimethyl oxalate, and the glycolide wherein $R^1$ and $R^2$ are both methyl.

10. The method of claim 1 wherein the ester is an oligomer formed from the reaction of oxalic acid and an alkylkene glycol and the alkylene glycol is selected from the group consisting of ethylene glycol, propylene glycol and 1,4-butanediol.

11. The method of claim 1 wherein the ester is incorporated into the polyamide backbone as single, diad, or triad units.

* * * * *